United States Patent

Hein

Patent Number: 5,396,989
Date of Patent: Mar. 14, 1995

[54] DIPWELL TRAY WITH MULTIPLICITY OF NEEDLE ORIENTING DIPWELLS

[75] Inventor: Gary L. Hein, Oakley, Ill.

[73] Assignee: Lincoln Diagnostics, Inc., Decatur, Ill.

[21] Appl. No.: 222,089

[22] Filed: Apr. 4, 1994

[51] Int. Cl.⁶ .......................................... B65D 83/02
[52] U.S. Cl. .................................. 206/366; 206/443; 206/564
[58] Field of Search ............... 206/210, 366, 365, 443, 206/564

[56] References Cited

U.S. PATENT DOCUMENTS

| | | | |
|---|---|---|---|
| 4,237,906 | 12/1980 | Havstad et al. | |
| 4,286,708 | 9/1981 | Porzel | 206/443 X |
| 4,681,219 | 7/1987 | Kitchens | 206/564 X |
| 4,722,440 | 2/1988 | Johnston | 206/564 X |
| 4,844,249 | 7/1989 | Coulombe | 206/366 X |
| 4,849,177 | 7/1989 | Jordan | 206/564 X |
| 5,084,028 | 1/1992 | Kennedy et al. | 206/366 X |
| 5,224,596 | 7/1993 | Kruger | 206/366 |

OTHER PUBLICATIONS

Aller/Guard Morrow Brown Disposable Allergy Test Needles-One-Sided Brochure.
Aller/Guard Morrow Brown Disposable Allergy Test Needles-Two-Sided Brochure.
Greer Laboratories, Inc. Greer DermaPIK System Brochure-Mar. 1992.

*Primary Examiner*—Jacob K. Ackun, Jr.
*Attorney, Agent, or Firm*—Lockwood, Alex, FitzGibbon & Cummings

[57] ABSTRACT

A dipwell tray for a variety of liquids to be selectively applied by sharp pointed needles to a person's skin. For example, the liquids may be antigens used in skin testing for allergies. The tray has a number of so-called dipwells with co-planar mouths or top openings. In use, the liquids are introduced into the dipwells and the needles are then inserted into the dipwells, making the set-up loaded and ready for the needles to be removed one-by-one with liquid adhering to their sharp points. In order to facilitate the removal of the needles the top openings of the dipwells are provided with oriented needle-receiving pockets whereby the needles in the dipwells will be inclined in a desired oriented direction.

5 Claims, 1 Drawing Sheet

DIPWELL TRAY WITH MULTIPLICITY OF NEEDLE ORIENTING DIPWELLS

BACKGROUND OF THE INVENTION

This invention relates, generally, to innovations and improvements in trays designed with a multiplicity of dipwells or similar relatively small containers for liquids. More specifically, the invention relates to such dipwell trays for holding a multiplicity of different liquids which are to be selectively applied by sharp pointed needles to the skin of individuals. For example, liquid antigens used in skin testing for allergies and which are applied to the skin of patients by means of sharp pointed needles.

While the dipwell trays of the present invention are particularly suited for embodying a multiplicity of dipwells for receiving a selection of liquid antigens to be used in skin testing for allergies with application being by sharp pointed needles, it will be understood that the dipwells may be used for containing other types of liquids to be applied to the skin by means of sharp pointed needles.

Using skin testing for allergies as a primary example, it is well known that in conducting such tests, a number of different antigens are applied to the skin one at a time by sharp pointed needles in a particular order of sequence by the person conducting the test. It is important in order that such tests can be carried out both accurately and expeditiously that the person conducting the skin test can proceed rapidly to remove a sharp pointed needle from each dipwell with a small amount of antigen adhering to the sharp points and apply it to a site on the skin of the patient in a predetermined sequence enabling the results of the test to be rapidly and accurately read.

The primary objective of the invention is to provide dipwell trays that include an array of needle-orienting dipwells that permit the person conducting a skin test to sequentially withdraw the needles from the dipwells rapidly and accurately without either skipping a needle or having a needle engage another needle.

The present invention provides a means whereby when dipwell trays are loaded with the desired variety of liquids and sharp pointed needles are inserted in the dipwells, the needles can be rapidly removed and used one-by-one because the handles or upper portions of the needles which project above the top openings of the dipwells are oriented in a predetermined direction. By having all of the needles oriented in a particular direction, the person removing the needles instinctively knows where to reach for and grasp the next needle to be removed almost without having to look. On the other hand, if the needles in the array of dipwells were inclined in random directions, the person removing them would have to take time to deliberately select and remove each needle, taking pains not to touch or disturb any of the adjacent needles. Furthermore, if the needles are not oriented in a particular direction there is a risk that a wrong needle may be removed and thereby the wrong antigen applied to a particular place on the skin where another antigen should have been applied, resulting in a flawed and misleading test.

Having in mind the above mentioned potential difficulties and possibilities for error, the importance will be understood and appreciated of providing dipwell trays for liquids to be applied to the skin by means of sharp pointed needles wherein when the needles are inserted in the dipwells in the loading procedure, they will automatically be oriented and retained in a predetermined oriented direction which materially facilitates the rapidity and accuracy with which they may be removed.

Certain other important objects of the invention will be apparent to those skilled in the art in light of the following detailed description of the invention taken in connection with the accompanying drawings wherein.

Figure 1:
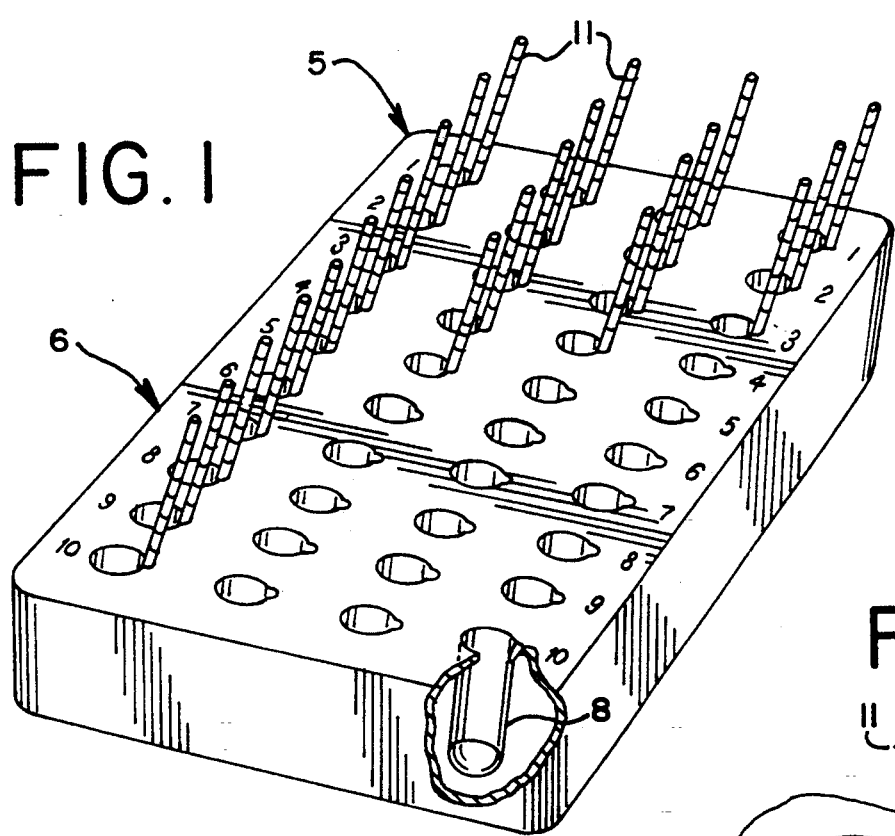
FIG. 1 is a top perspective view, partly broken away, of a dipwell tray embodying the present invention showing a plurality of sharp pointed needles in the dipwells all oriented in a predetermined direction by means of needle-retaining pockets formed in the top openings or mouths of the individual dipwells.
Figure 2:
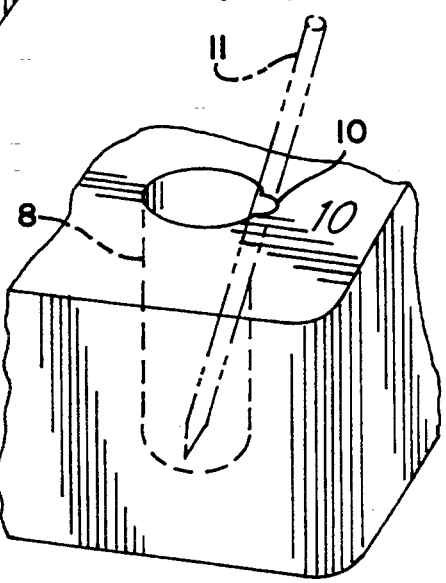
FIG. 2 is a fragmentary perspective view on enlarged scale of showing the dipwell in the broken away corner of FIG. 1 with an inclined needle in place therein.

Referring to the drawings, a dipwell tray is indicated generally at 5 which may be in the form of a rectangular open box indicated generally at 6 embodying an array of test tube shaped dipwells 8—8. The box 6 and dipwells 8 may be integrally formed by injection molding. The mouths or top openings of each dipwell 8 may be circular except for the provision of a small needle receiving notch or pocket 10 formed at one location for receiving and retaining the stem of a sharp pointed needle 11 of known type such as a vaccinating needle.

In the particular embodiment shown there are 40 dipwells 8 being arrayed in four rows A, B, C and D of ten containers each. For the convenience of the person conducting a skin test or otherwise using the sharp pointed needles 11—11 the top surface of the box 6 has the rows identified by letters A, B, C and D and the dipwells in each row numbered 1 through 10, as shown.

As an alternative to an integrally formed dipwell tray, the top of a box may be provided with a corresponding array of circular openings for receiving individually formed dipwells with needle receiving pockets. In order to facilitate oriented insertion of the individual dipwells such circular openings may have oriented notches to receive the needle orienting pockets of the dipwells.

When the time comes to load the dipwells 8 in a tray 5 with antigens, the desired antigens or other liquids are introduced into the respective dipwells 8 and then the needles 11 are inserted in the dipwells so as to rest in the pockets or notches 10 as described above. It is important that the pockets 10 of the dipwells 8 be oriented in the same predetermined direction so that when the needles 10 are inserted into the dipwells they will all be inclined in the same predetermined direction.

With the tray 5 being thus loaded with liquids and needles and ready for use, the administrator of the test may first remove needles 11 from the dipwells 8 in column A starting with dipwell A1 and proceeding sequentially through dipwell A10. In the same manner, the administrator of the test proceeds to remove and use the needles 11 in rows B, C and D. Since all of the needles 11 are tilted and oriented in the same direction, the user can readily reach for and grasp the next needle to be removed with a minimum of distraction. In fact, with practice, an administrator will be able to remove the needles in the proper order almost without having to observe which needle is being removed. On the other hand, it will be seen that if the needles were not so oriented, the administrator would have to carefully remove each needle taking pains not to disturb a needle in an adjoining dipwell.

Figure 4:
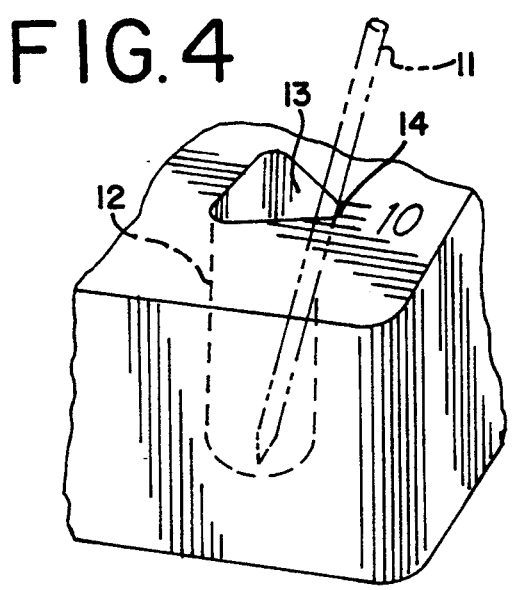
FIG. 4 is a view corresponding to FIG. 2 but showing a dipwell having a triangular mouth.
Figure 3:
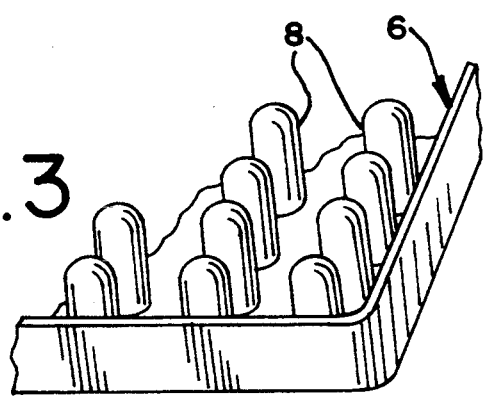
FIG. 3 is a fragmentary perspective view of the underside of one corner of dipwell tray shown in FIG. 1.

Instead of using dipwells 8 that have circular mouths with notches or pockets 10 at one location in the circumference, other shapes may be utilized for providing the pockets to receive and retain the needles 11 in oriented array. Referring to FIG. 4, a dipwell 12 is shown therein having a triangular body and mouth or top opening 13 with a corner 14 of the top mouth oriented in the desired direction and a sharp pointed needle 11 inserted therein in tilted condition. It will be understood that dipwells having mouths or top openings of other shapes may be used such as square, rectangular or elliptical.

What is claimed is:

1. In a dipwell tray for holding a variety of liquids to be applied in a predetermined order by sharp pointed needles to a person's skin, such tray having a multiplicity of dipwells with co-planar top openings for holding said liquids, such tray further having a sharp pointed needle resting in each dipwell and having a substantial portion of its length projecting above the dipwell top opening, each said top opening having a "needle orienting pocket in which said needles rest," each needle being retained in a dipwell by a said pocket in an inclined or tilted position and oriented in the same direction.

2. The tray of claim 1 wherein each said pocket has arcuate needle-engaging sides.

3. The tray of claim 1 wherein each said pocket is the vertex of an angle.

4. The dipwell tray of claim 1 wherein said dipwells are arrayed in a plurality of parallel rows.

5. The tray of claim 4 wherein the body of said tray is in the form of a box having a top wall into which said dipwells are integrally formed.

* * * * *